US010813859B2

United States Patent
Saitoh et al.

(10) Patent No.: US 10,813,859 B2
(45) Date of Patent: Oct. 27, 2020

(54) WRINKLE AMELIORATING AGENT

(71) Applicant: POLA CHEMICAL INDUSTRIES, INC., Fukuroi-shi, Shizuoka (JP)

(72) Inventors: Yuko Saitoh, Yokohama (JP); Mayumi Shishido, Yokohama (JP)

(73) Assignee: POLA CHEMICAL INDUSTRIES, INC., Fukuroi-Shi, Shizuoka (JP)

(*) Notice: Subject to any disclaimer, the term of this patent is extended or adjusted under 35 U.S.C. 154(b) by 0 days.

(21) Appl. No.: 16/464,212

(22) PCT Filed: Nov. 27, 2017

(86) PCT No.: PCT/JP2017/042345
§ 371 (c)(1),
(2) Date: May 24, 2019

(87) PCT Pub. No.: WO2018/097277
PCT Pub. Date: May 31, 2018

(65) Prior Publication Data
US 2019/0388313 A1 Dec. 26, 2019

(30) Foreign Application Priority Data
Nov. 28, 2016 (JP) ................................ 2016-230435

(51) Int. Cl.
| A61K 8/34 | (2006.01) |
| A61K 8/06 | (2006.01) |
| A61K 8/25 | (2006.01) |
| A61K 8/362 | (2006.01) |
| A61K 8/368 | (2006.01) |
| A61K 8/49 | (2006.01) |
| A61K 8/60 | (2006.01) |
| A61K 8/73 | (2006.01) |
| A61K 8/86 | (2006.01) |
| A61K 8/92 | (2006.01) |

(52) U.S. Cl.
CPC .............. *A61K 8/345* (2013.01); *A61K 8/062* (2013.01); *A61K 8/064* (2013.01); *A61K 8/25* (2013.01); *A61K 8/34* (2013.01); *A61K 8/362* (2013.01); *A61K 8/368* (2013.01); *A61K 8/498* (2013.01); *A61K 8/60* (2013.01); *A61K 8/73* (2013.01); *A61K 8/86* (2013.01); *A61K 8/922* (2013.01); *A61K 8/925* (2013.01)

(58) Field of Classification Search
CPC .... A61K 2300/00; A61K 31/19; A61K 31/20; A61K 2800/524; A61K 2800/596; A61K 2800/87; A61K 8/0208; A61K 8/11; A61K 8/361; A61K 8/365; A61K 8/368; A61K 8/416; A61K 8/8129; A61K 8/8135; A61K 8/92
See application file for complete search history.

(56) References Cited

U.S. PATENT DOCUMENTS

| 2003/0152644 A1 | 8/2003 | Modak et al. |
| 2010/0292509 A1 | 11/2010 | Kajiya et al. |
| 2017/0156999 A1* | 6/2017 | Harris ................ A61Q 19/10 |

FOREIGN PATENT DOCUMENTS

| FR | 2927804 A1 | 8/2009 |
| JP | 2007-291049 A | 11/2007 |
| JP | 2011-057647 A | 3/2011 |
| JP | 2011-173808 A | 9/2011 |
| WO | WO 2009/093534 A1 | 7/2009 |

OTHER PUBLICATIONS

International Search Report issued in International Patent Application No. PCT/JP2017/042345 dated Jan. 16, 2018.
Transmittal of Translation of the International Preliminary Report on Patentability issued in International Patent Application No. PCT/JP2017/042345 dated May 28, 2019.
Adeka Corporation, Adeka NOL CHG, Technical Information Jun. 9, 2016, pp. 1-7, available at https://www.adeka.co.jp/chemical/catalog/pdf/adeka_CHG.pdf.
EESR issued in corresponding European Patent Application No. 17873602.1 dated Jun. 8, 2020.

* cited by examiner

*Primary Examiner* — Nannette Holloman
(74) *Attorney, Agent, or Firm* — Knobbe, Martens, Olson & Bear LLP

(57) ABSTRACT

The object is to provide a wrinkle improving agent having an excellent wrinkle improving effect. A compound expressed by the following Formulas (1) and/or (2) is used as an active ingredient of a wrinkle improving agent.

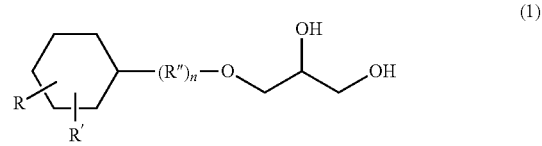

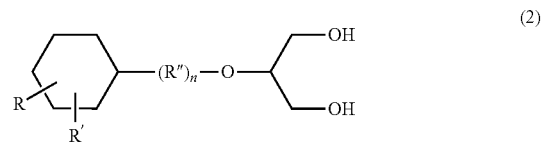

(In Formulas (1) and (2), R and R' independently represent a hydrogen atom or an alkyl group having 1 to 4 carbon atoms, R" represents an alkylene group having 1 to 3 carbon atoms, and n represents a number of 0 or 1.)

4 Claims, 5 Drawing Sheets

WRINKLE AMELIORATING AGENT

TECHNICAL FIELD

The present invention relates to a wrinkle improving agent having an excellent wrinkle improving effect.

BACKGROUND ART

The wrinkle is one of skin aging symptoms caused by aging, stress, exposure to ultraviolet rays, or the like, which greatly affects the impression of a face because it is easily recognizable. Therefore, interest in wrinkle and its improvement method is very high.

Conventionally, a moisturizing means using an external preparation for skin containing a polymer having a water retention capacity such as mucopolysaccharide or collagen has been adopted to improve wrinkles. However, it alone could not improve wrinkles sufficiently.

The mechanism of wrinkle formation is complicated, and it is difficult to replicate it experimentally, so the mechanism has not been fully elucidated even now. Nonetheless, in recent studies, it has become clear that not only aging is an important factor, but also drying, oxidation, glycosylation, ultraviolet rays, etc. are factors that affect greatly skin aging symptoms. Specifically, the factors, especially exposure to ultraviolet rays, cause cell damage and thereby enhanced apoptosis of cells, decrease in the turnover rate of a fibrillary element such as collagen due to decline in the proliferation activity of fibroblasts, which are the principal cells in the dermis, or in the synthesis function of collagen, etc., collapse of a fiber bundle due to increase in inflammatory cytokine, accumulation of waste matter due to reduction of the vascular system, decrease in nutrient supply, and the like. As a result, the elasticity of the skin is conceivably lost to generate wrinkles.

Since there are many factors which have influences on the mechanism of generation of wrinkles in complicated manners as described above, various ingredients have been proposed for a wrinkle improving agent. For example, it is known that retinol and its metabolite retinoic acid, an amino acid, such as alanine and glycine, a macromolecule, such as collagen and hyaluronic acid, ascorbic acid, tocopherol, and the like have a wrinkle improving effect. Further, it has been reported that a tranexamic acid amide derivative can also promote production of vascular endothelial growth factor C, and can become an active ingredient of a wrinkle improving agent (Patent Literature 1).

However, the wrinkle improvement effect of the conventional wrinkle improving agent was not fully satisfactory, or brought about in some cases undesirable other effects (side reactions) at a concentration effective in exerting the wrinkle improving effect. Therefore, there is a demand for a new ingredient that exerts a wrinkle improvement effect.

In this regard, it has been confirmed that the glycerol derivative described in Patent Literature 2 has antibacterial action equal to or higher than that of paraben, and high safety, and application to cosmetics and detergents has been proposed.

CITATION LIST

Patent Literature

[Patent Literature 1] International Publication No. WO 2009/093534

[Patent Literature 2] Japanese Unexamined Patent Application Publication No. 2007-291049

SUMMARY OF INVENTION

Technical Problem

An object of the present invention is to provide a wrinkle improving agent having an excellent wrinkle improving effect.

Solution to Problem

The present inventors conducted intensive studies in search of a compound having a wrinkle improving effect to find that a glycerol derivative having a specific structure is highly safe to the skin, and exerts an excellent anti-wrinkle action, thereby completing the present invention.

That is, an aspect of the present invention is a wrinkle improving agent comprising a compound expressed by the following Formula (1), and/or Formula (2).

[Chem. 1]

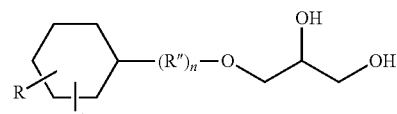

(1)

[Chem. 2]

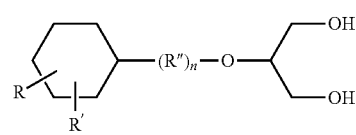

(2)

(In Formulas (1) and (2), R and R' independently represent a hydrogen atom or an alkyl group having 1 to 4 carbon atoms, R" represents an alkylene group having 1 to 3 carbon atoms, and n represents a number of 0 or 1.)

Another aspect of the present invention is an external composition for skin for wrinkle improvement containing the wrinkle improving agent. The external composition for skin is preferably a cosmetic.

Advantageous Effects of Invention

According to the present invention, a wrinkle improving agent having high safety to the skin and an excellent wrinkle improving effect is provided. In addition, an external composition for skin for wrinkle improvement containing the wrinkle improving agent is also provided, which is suitable as cosmetic. Such an external composition for skin is in line with the trend of the times expecting an anti-aging effect from a cosmetic, and it meets the needs of consumers.

DESCRIPTION OF EMBODIMENTS

Figure 1:
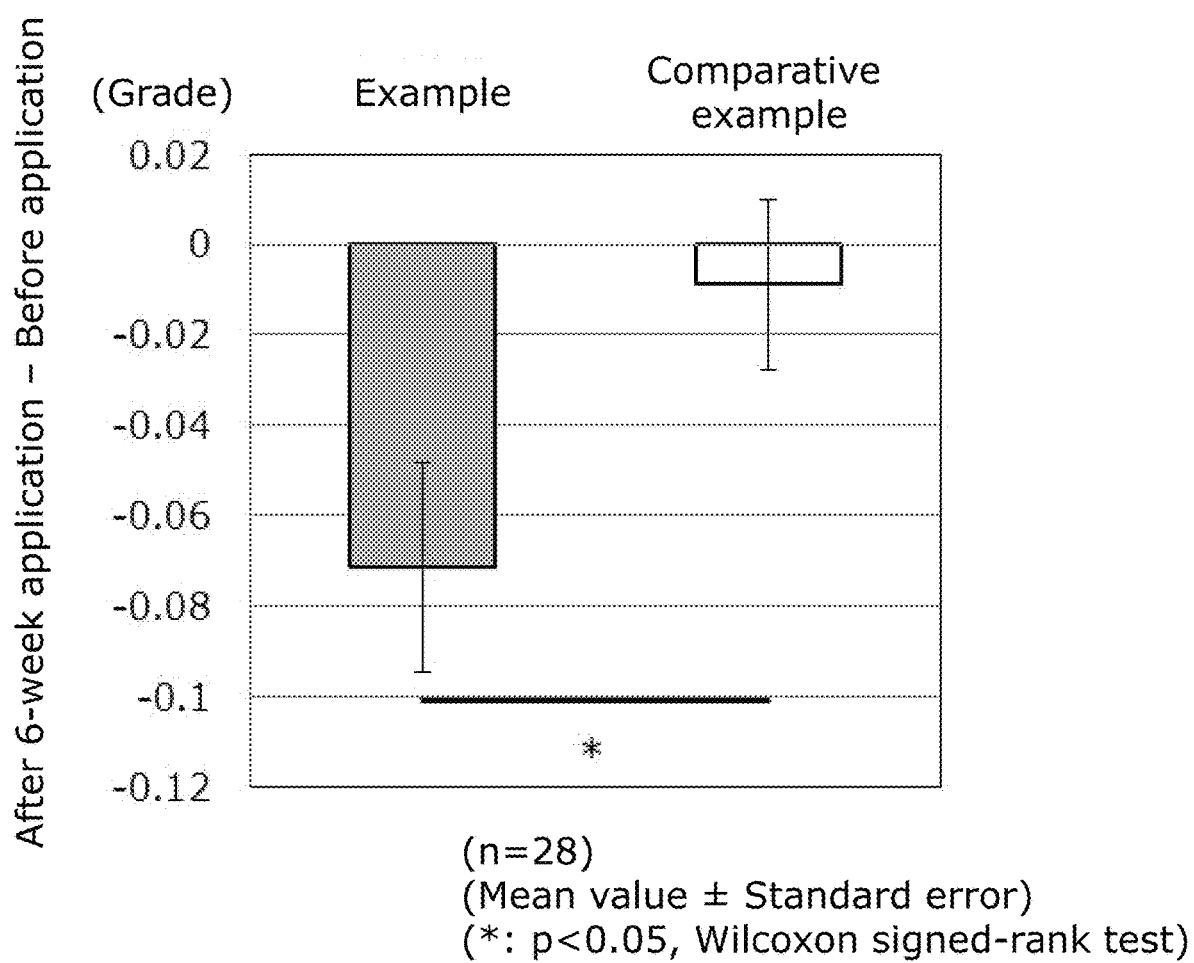
FIG. 1 is a graph showing a wrinkle grade by photographic rating of a formulation application site.

The wrinkle improving agent of the present invention contains a compound expressed by the following Formulas (1) and/or (2).

[Chem. 3]

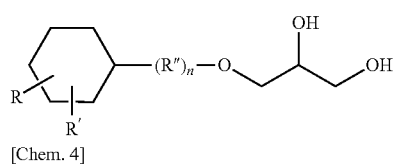
(1)

[Chem. 4]

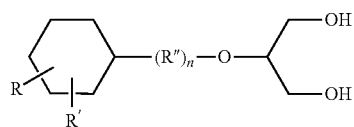
(2)

In Formulas (1) and (2), R and R' independently represent a hydrogen atom, or an alkyl group having 1 to 4 carbon atoms.

Examples of the alkyl group having 1 to 4 carbon atoms include a methyl group, an ethyl group, a propyl group, an isopropyl group, a butyl group, an isobutyl group, a sec-butyl group, and a tert-butyl group. Among them, since the wrinkle improving action is good, R and R' independently are preferably a hydrogen atom, or an alkyl group having 1 to 2 carbon atoms, more preferably a hydrogen atom or a methyl group, and further preferably a hydrogen atom. Although R and R' may be the same or different, one of them is preferably a hydrogen atom, and more preferably both of them are a hydrogen atom, because the wrinkle improving action is good.

Although there is no particular restriction on the positions of R and R', when either one is a hydrogen atom, the other takes preferably the 4-position.

In Formulas (1) and (2), R″ represents an alkylene group having 1 to 3 carbon atoms. Examples of the alkylene group having 1 to 3 carbon atoms include a methylene group, an ethylene group, a propylene group, and an isopropylene group, and among them a methylene group and an ethylene group are preferable.

In Formulas (1) and (2), n represents a number of 0 or 1, and from the viewpoint of better availability of the compound, 0 is preferable.

Examples of such a compound represented by Formula (1) include 3-cyclohexyloxy-1,2-propanediol, 3-(2-methylcyclohexyloxy)-1,2-propanediol, 3-(3-methylcyclohexyloxy)-1,2-propanediol, 3-(4-methylcyclohexyloxy)-1,2-propanediol, 3-(2-ethylcyclohexyloxy)-1,2-propanediol, 3-(3-ethylcyclohexyloxy)-1,2-propanediol, 3-(4-ethylcyclohexyloxy)-1,2-propanediol, 3-(2,3-dimethylcyclohexyl oxy)-1,2-propanediol, 3-(2,4-dimethylcyclohexyloxy)-1,2-propanediol, 3-(2,5-dimethylcyclohexyloxy)-1,2-propanediol, 3-(2,6-dimethylcyclohexyloxy)-1,2-propanediol, 3-(3,4-dimethylcyclohexyloxy)-1,2-propanediol, 3-(3,5-dimethylcyclohexyloxy)-1,2-propanediol, 3-(2-propylcyclohexyloxy)-1,2-propanediol, 3-(3-propylcyclohexyloxy)-1,2-propanediol, 3-(4-propylcyclohexyloxy)-1,2-propanediol, 3-(2-isopropylcyclohexyloxy)-1,2-propanediol, 3-(3-isopropylcyclohexyloxy)-1,2-propanediol, 3-(4-isopropylcyclohexyloxy)-1,2-propanediol, 3-(2-t-butylcyclohexyloxy)-1,2-propanediol, 3-(3-t-butylcyclohexyloxy)-1,2-propanediol, 3-(4-t-butylcyclohexyloxy)-1,2-propanediol, 3-(2-methyl-5-isopropylcyclohexyloxy)-1,2-propanediol, 3-(5-methyl-2-isopropylcyclohexyloxy)-1,2-propanediol, 3-(4-methylcyclohexylmethoxy)-1,2-propanediol, 3-(1-cyclohexylpropyloxy)-1,2-propanediol, 3-(2-cyclohexylpropyloxy)-1,2-propanediol, 3-(3-cyclohexylpropyloxy)-1,2-propanediol, 3-(2-cyclohexyl-1-methylethoxy)-1,2-propanediol, 3-(2,4-dimethylcyclohexylmethoxy)-1,2-propanediol, and 3-(3,5-dimethylcyclohexylmethoxy)-1,2-propanediol.

Examples of such a compound represented by Formula (2) include 2-cyclohexyloxy-1,3-propanediol, 2-(2-methylcyclohexyloxy)-1,3-propanediol, 2-(3-methylcyclohexyloxy)-1,3-propanediol, 2-(4-methylcyclohexyloxy)-1,3-propanediol, 2-(2-ethylcyclohexyloxy)-1,3-propanediol, 2-(3-ethylcyclohexyloxy)-1,3-propanediol, 2-(4-ethylcyclohexyloxy)-1,3-propanediol, 2-(2,3-dimethylcyclohexyloxy)-1,3-propanediol, 2-(2,4-dimethylcyclohexyloxy)-1,3-propanediol, 2-(2,5-dimethylcyclohexyloxy)-1,3-propanediol, 2-(2,6-dimethylcyclohexyloxy)-1,3-propanediol, 2-(3,4-dimethylcyclohexyloxy)-1,3-propanediol, 2-(3,5-dimethylcyclohexyloxy)-1,3-propanediol, 2-(2-propylcyclohexyloxy)-1,3-propanediol, 2-(3-propylcyclohexyloxy)-1,3-propanediol, 2-(4-propylcyclohexyloxy)-1,3-propanediol, 2-(2-isopropylcyclohexyloxy)-1,3-propanediol, 2-(3-isopropylcyclohexyloxy)-1,3-propanediol, 2-(4-isopropylcyclohexyloxy)-1,3-propanediol, 2-(2-t-butylcyclohexyloxy)-1,3-propanediol, 2-(3-t-butylcyclohexyloxy)-1,3-propanediol, 2-(4-t-butylcyclohexyloxy)-1,3-propanediol, 2-(2-methyl-5-isopropylcyclohexyloxy)-1,3-propanediol, 2-(5-methyl-2-isopropylcyclohexyloxy)-1,3-propanediol, 2-(4-methylcyclohexylmethoxy)-1,3-propanediol, 2-(1-cyclohexylpropyloxy)-1,3-propanediol, 2-(2-cyclohexylpropyloxy)-1,3-propanediol, 2-(3-cyclohexylpropyloxy)-1,3-propanediol, 2-(2-cyclohexyl-1-methylethoxy)-1,3-propanediol, 2-(2,4-dimethylcyclohexylmethoxy)-1,3-propanediol, and 2-(3,5-dimethylcyclohexylmethoxy)-1,3-propanediol.

Among them, 3-cyclohexyloxy-1,2-propanediol, 3-(2-methylcyclohexyloxy)-1,2-propanediol, 3-(3-methylcyclohexyloxy)-1,2-propanediol, 3-(4-methylcyclohexyloxy)-1,2-propanediol, 3-(2-isopropylcyclohexyloxy)-1,2-propanediol, 3-(2-t-butylcyclohexyloxy)-1,2-propanediol, 3-cyclohexylmethoxy-1,2-propanediol, 3-cyclohexylethoxy-1,2-propanediol, 3-cyclohexyloxy-1,3-propanediol, 2-(2-methylcyclohexyloxy)-1,3-propanediol, 2-(3-methylcyclohexyloxy)-1,3-propanediol, 2-(4-methylcyclohexyloxy)-1,3-propanediol, 2-(2-isopropylcyclohexyloxy)-1,3-propanediol, 2-(2-t-butylcyclohexyloxy)-1,3-propanediol, 2-cyclohexylmethoxy-1,3-propanediol, and 2-cyclohexylethoxy-1,3-propanediol are more preferable; 3-cyclohexyloxy-1,2-propanediol, 3-(3-methylcyclohexyloxy)-1,2-propanediol, 3-(4-methylcyclohexyloxy)-1,2-propanediol, and 3-cyclohexylmethoxy-1,2-propanediol are further preferable; and 3-cyclohexyloxy-1,2-propanediol (Compound 1) is particularly preferable.

[Chem. 5]

(Compound 1)

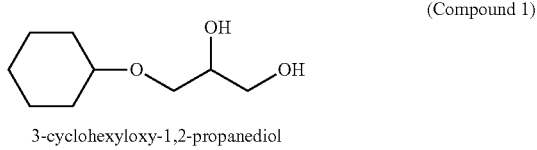

3-cyclohexyloxy-1,2-propanediol

The compound represented by Formula (1) or (2) can be obtained through synthesis and purification by a conventional method. For example, it can be synthesized by the reaction described in Patent Literature 2 or the like, and can be produced through appropriate isolation and purification methods.

Since the compound expressed by Formula (1) or (2) has an excellent wrinkle improving effect, the same constitutes an active ingredient of a wrinkle improving agent.

The term "wrinkle improvement" means herein that skin grooves become shallow, thin, or short and wrinkles become less conspicuous.

From another viewpoint, the present invention may be understood as a method for wrinkle-improving comparing application of a compound expressed by Formulas (1) and/or (2).

From another viewpoint, the present invention may be understood as a use of a compound expressed by Formulas (1) and/or (2) for improving the wrinkle.

From another viewpoint, the present invention may be understood as a use of a compound expressed by Formulas (1) and/or (2) for producing a wrinkle improving agent.

From another viewpoint, the present invention may be understood as a compound expressed by Formulas (1) and/or (2) used for improving the wrinkle.

As shown in Example to be described later, the wrinkle improving agent of the present invention has an effect of reducing the depth, width, or length of the wrinkle, and in particular, an effect of making not only fine wrinkles caused by drying, but also deep wrinkles caused by aging less conspicuous.

It is presumed that such a wrinkle improving effect is derived from the moisturizing effect caused by a high moisture absorbing property of a glycerol skeleton, as shown in the test examples described later, which is owned by the compound represented by Formula (1) or (2). In addition, since the wrinkle improving agent is also effective for an age-related wrinkle caused by a factor other than drying, it is presumed that there exists a mechanism to improve wrinkles, in which the moisture content in the stratum corneum and the flexibility of the stratum corneum are increased by some effect of the compound, such as a hyaluronan synthesis promoting effect. In the test examples described later, it has been confirmed that the compound increases the expression level of the hyaluronan synthetase gene.

A wrinkle improving agent of the present invention may be contained in a wrinkle improving composition, and particularly preferably in an external composition for skin, from which an effect can be expected by percutaneous absorption. There is no particular restriction on the form of the external composition for skin, insofar as it can be applied to the skin externally, and preferable examples thereof include a cosmetic (including a quasi-drug), and medicinal products. Since high safety has been confirmed with respect to the compounds expressed by Formula (1) or (2), the same may be continuously applied in the form of a cosmetic which is routinely used.

There is no particular restriction on the formulation of the external composition for skin, and examples thereof include a lotion formulation, an emulsion formulation (O/W type, W/O type, etc.), such as milky lotion or cream, an oil formulation, a gel formulation, a pack, and a cleanser.

In a case where a wrinkle improving agent of the present invention is blended in a wrinkle improving external composition for skin, when the total amount of the compounds represented by Formulas (1) and/or (2) with respect to the total amount of the composition is preferably from 0.01% to 10% by mass, and more preferably from 0.1 to 2% by mass, a desired effect can be easily obtained, and the design flexibility of the recipe can be secured.

An external composition for skin for improving the wrinkle according to the present invention may optionally contain ingredients to be incorporated commonly in an external composition for skin in addition to a wrinkle improving agent of the present invention to the extent that the advantageous effects of Invention are not impaired.

Examples of such ingredients include an oil and wax, such as a macadamia nut oil, an avocado oil, a corn oil, an olive oil, a rapeseed oil, a sesame oil, a castor oil, a safflower oil, a cottonseed oil, a jojoba oil, a coconut oil, a palm oil, a liquid lanolin, a hydrogenated coconut oil, a hydrogenated oil, a Japan wax, a hydrogenated castor oil, a bees wax, a candelilla wax, a carnauba wax, an insect wax, lanolin, a reduced lanolin, a hard lanolin, and a jojoba wax; a hydrocarbon, such as liquid paraffin, squalane, pristane, ozokerite, paraffin, ceresin, petrolatum, and a microcrystalline wax; a higher fatty acid, such as oleic acid, isostearic acid, lauric acid, myristic acid, palmitic acid, stearic acid, behenic acid, and undecylenic acid; a higher alcohol, such as cetyl alcohol, stearyl alcohol, isostearyl alcohol, behenyl alcohol, octyldodecanol, myristyl alcohol, and cetostearyl alcohol; a synthetic ester oil, such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethylhexanoate, neopentyl glycol dicaprate, glycerol di-2-heptylundecanoate, glycerol tri-2-ethylhexanoate, trimethylolpropane tri-2-ethylhexanoate, trimethylolpropane triisostearate, and pentaerythrit tetra-2-ethylhexanoate; an open-chain polysiloxane, such as dimethylpolysiloxane, methylphenylpolysiloxane, and diphenylpolysiloxane; a cyclic polysiloxane, such as octamethylcyclotetrasiloxane, decamethylcyclopentasiloxane, and dodecamethylcyclohexasiloxane; and an oil like a silicone oil as a modified polysiloxane, such as an amino-modified polysiloxane, a polyether-modified polysiloxane, an alkyl-modified polysiloxane, and a fluorine-modified polysiloxane;

An anionic surfactant, such as fatty acid soap (sodium laurate, sodium palmitate, etc.), potassium lauryl sulfate, and triethanolamine alkyl ether sulfate; a cationic surfactant, such as stearyl trimethyl ammonium chloride, benzalkonium chloride, and lauryl amine oxide; an amphoteric surfactant, such as an imidazoline type amphoteric surfactant (2-cocoyl-2-imidazolinium hydroxide-1-carboxyethyloxy disodium salt, etc.), a betaine type surfactant (alkylbetaine, amidobetaine, sulfobetaine, etc.), and acylmethyltaurine; a nonionic surfactant, such as a sorbitan fatty acid ester (sorbitan monostearate, sorbitan sesquioleate, etc.), a glycerol fatty acid (glycerol monostearate, etc.), a propylene glycol fatty acid ester (propylene glycol monostearate, etc.), a hydrogenated castor oil derivative, a glycerol alkyl ether, a POE sorbitan fatty acid ester (POE sorbitan monooleate, polyoxyethylene sorbitan monostearate, etc.), a POE sorbit fatty acid ester (POE-sorbit monolaurate, etc.), a POE glycerol fatty acid ester (POE glycerol monoisostearate, etc.), a POE fatty acid ester (polyethylene glycol monooleate, POE distearate, etc.), a POE alkyl ether (POE 2-octyldodecyl ether, etc.), a POE alkylphenyl ether (POE nonylphenyl ether, etc.). Pluronic series, a POE-POP alkyl ether (POE-POP 2-decyltetradecyl ether, etc.), Tetronic series, a POE castor oil or hydrogenated castor oil derivative (POE castor oil, POE hydrogenated castor oil, etc.), a sucrose fatty acid ester, and an alkyl glucoside; a polyhydric alcohol, such as Poly(ethylene glycol), glycerol, 1,3-butylene glycol, erythritol, sorbitol, xylitol, maltitol, propylene glycol, dipropylene glycol, diglycerol, isoprene glycol, 1,2-pentanediol, 2,4-hexanediol, 1,2-hexanediol, and 1,2-octanediol;

A moisturizing component, such as sodium pyrrolidone carboxylate, lactic acid, and sodium lactate; a powder, which may be optionally surface-treated, such as mica, talc, kaolin, synthetic mica, calcium carbonate, magnesium carbonate, anhydrous silicic acid (silica), aluminum oxide, and barium sulfate; an inorganic pigment, which may be optionally surface-treated, such as Bengal red, yellow iron oxide, black iron oxide, cobalt oxide, ultramarine blue, iron blue, titanium oxide, and zinc oxide; a pearling agent, which may be optionally surface-treated, such as titanated mica, fish scale flake, and bismuth oxychloride; an organic dye, which may be optionally laked, such as Red No. 202, Red No. 228, Red No. 226, Yellow No. 4, Blue No. 404, Yellow No. 5, Red No. 505, Red No. 230, Red No. 223, Orange No. 201. Red No. 213. Yellow No. 204, Yellow No. 203, Blue No. 1, Green No. 201, Violet No. 201, and Red No. 204; an organic powder, such as a polyethylene powder, poly(methyl methacrylate), a nylon powder, and an organopolysiloxane elastomer; a p-aminobenzoic acid type ultraviolet absorber: an anthranilic acid type ultraviolet absorber; a salicylic acid type ultraviolet absorber; a cinnamic acid type ultraviolet absorber; a benzophenone type ultraviolet absorber; a sugar type ultraviolet absorber; an ultraviolet absorber, such as 2-(2'-hydroxy-5'-t-octylphenyl)benzotriazole, and 4-methoxy-4'-t-butyldibenzoylmethane:

A lower alcohol, such as ethanol, and isopropanol; a vitamin B, such as vitamin A or its derivatives, vitamin B or its derivatives, vitamin $B_6$ hydrochloride, vitamin $B_6$ tripalmitate, vitamin $B_6$ dioctanoate, vitamin $B_2$ or its derivatives, vitamin $B_{12}$, and vitamin $B_{15}$ or its derivatives; a vitamin, a vitamin E, such as α-tocopherol, β-tocopherol, γ-tocopherol, and vitamin E acetate; other vitamins, such as a vitamin D, vitamin H, pantothenic acid, pantethine, and pyrroloquinoline quinone; an antimicrobial agent (preservative), such as methylparaben, ethylparaben, butylparaben, and phenoxyethanol; an anti-inflammatory agent, such as a glycyrrhizic acid derivative, a glycyrrhetinic acid derivative, a salicylic acid derivative, hinokitiol, zinc oxide, and allantoin; a whitening agent, such as an alkylresorcinol, a placenta extract, a saxifrage extract, and arbutin; various extracts (e.g., Phellodendron bark, Coptis Rhizome, Lithospermi radix, peony root, swertia herb, birch, sage, loquat, carrot, aloe, mallow, iris, grape, coix seed, loofah, lily, saffron, cnidium rhizome, ginger, Hypericum, Ononis, garlic. Capsicum, Citrus Unshiu peel, Japanese Angelica root, and seaweed, etc.; an activator, such as royal jelly, a photosensitizer, and a cholesterol derivative; a blood circulation promoter, such as nonylic acid vanillylamide, capsaicin, zingelon, and tannic acid; an antiseborrheic agent, such as sulfur, and thianthol; an anti-inflammatory agent, such as tranexamic acid, thiotaurine, and hypotaurine; and a water-soluble polymer, such as collagen and hyaluronic acid.

Further, a wrinkle improving agent other than the wrinkle improving agent of the present invention may be blended together in the external composition.

EXAMPLE

The present invention will be described in more detail below with reference to concrete experimental examples, provided that the present invention is not limited to the following aspects.

<Wrinkle Improving Effect Confirmation Test>

Cosmetics of Example and Comparative Example described in Table 1 were prepared respectively in a conventional manner.

Total 28 healthy Japanese women aged from 35 to 55 and having wrinkles of wrinkle grade 2 to 4 (average 3.1) described later were asked to apply the prepared cosmetic of Example to a half of face and apply the cosmetic of Comparative Example to the other half of face respectively twice a day for 6 weeks.

The wrinkle improving effect of each cosmetic was evaluated by the following tests (1) to (4). Further, according to the test (5), occurrence of an adverse event by application of each cosmetic was observed.

TABLE 1

|  | Example | (% by mass) Comparative Example |
|---|---|---|
| Compound 1 | 0.5 | — |
| Ethanol | 3 | 3 |
| 1,3-Butylene glycol | 8 | 8 |
| Methyl p-hydroxybenzoate | 0.2 | 0.2 |
| Glycerol | 5 | 5 |
| Polyoxyethylene hydrogenated castor oil | 0.05 | 0.05 |
| Citric acid | 0.01 | 0.01 |
| Sodium citrate | 0.1 | 0.1 |
| Water | balance | balance |

(1) Wrinkle Grade Rating

The left and right corners of the eyes of each of the subjects were photographed using a digital camera before and after the application period. The chin and the forehead of a subject sitting on a chair and closing the eyes gently were fixed with a fixation rack, and the left and right corners of the eyes were photographed from the front side diagonally at 45 degrees. The wrinkle grades were rated based on the photographs according to the following criteria published in Journal of Japanese Cosmetic Science Society Vol. 30, No. 4, pp. 316-322, and the difference between before the application and after the 6-week application was calculated. The mean values of all the test subjects are shown in FIG. 1 with respect to the cosmetics of the Example and Comparative Example.

Wrinkle Grade:
0: There is no wrinkle.
1: Indistinct shallow wrinkle is slightly recognized.
2: Distinct shallow wrinkle is slightly recognized.
3: Distinct shallow wrinkle is recognized.
4: Slightly deep wrinkle is slightly recognized among distinct shallow wrinkles.
5: Slightly deep wrinkle is recognized.
6: Distinct deep wrinkle is recognized.
7: Notably deep wrinkle is recognized.

(2) Replica Analysis

Figure 2:
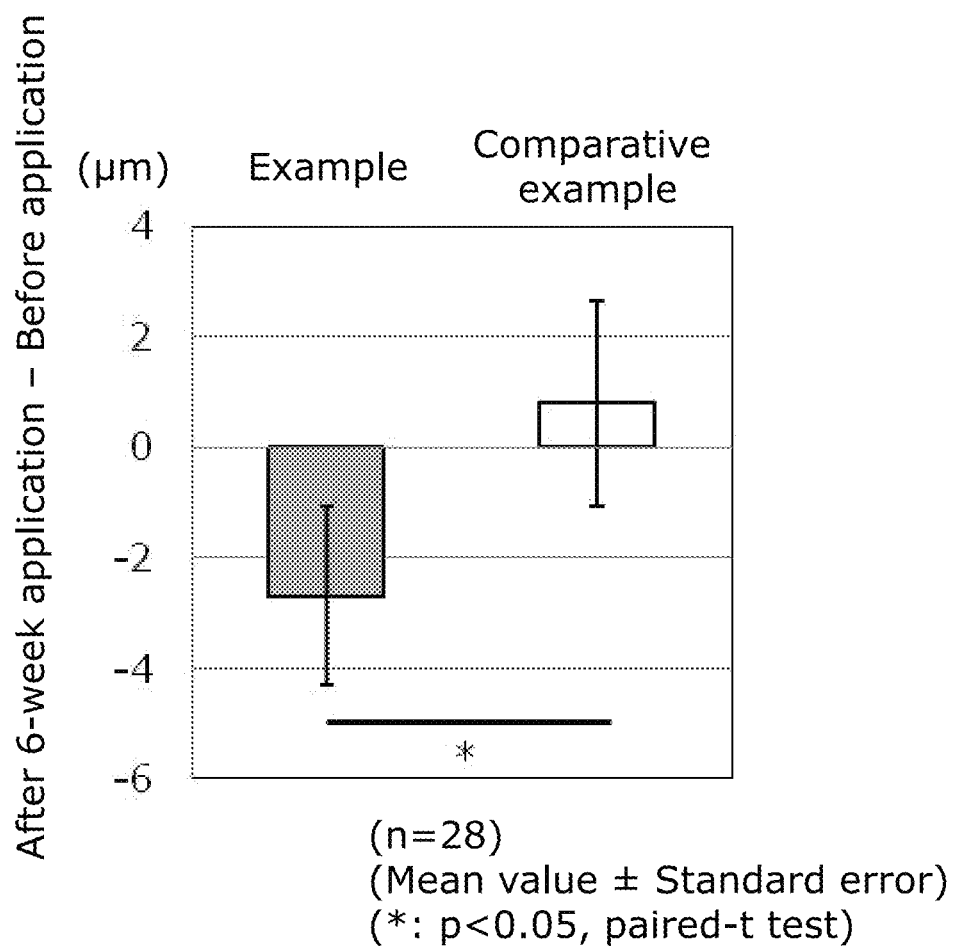
FIG. 2 is a graph showing the maximum depth of the maximum wrinkle by replica analysis of a formulation application site.

Before and after the application period, an impression of the skin surface profile at the left and right corners of the eyes using a replica agent (SILFLO; produced by Cuderm Corporation) by a conventional method to prepare a replica. The maximum depth of the maximum wrinkle in the replica produced was measured using a two-dimensional image analysis system (Image-Pro Plus v.7 software; produced by Media Cybemetics, Inc.), and the difference between before the application and after the 6-week application was calculated. The mean values of all the test subjects are shown in FIG. 2 with respect to the cosmetics of the Example and Comparative Example.

(3) Measurement of Moisture Content in Stratum Corneum

Figure 3:
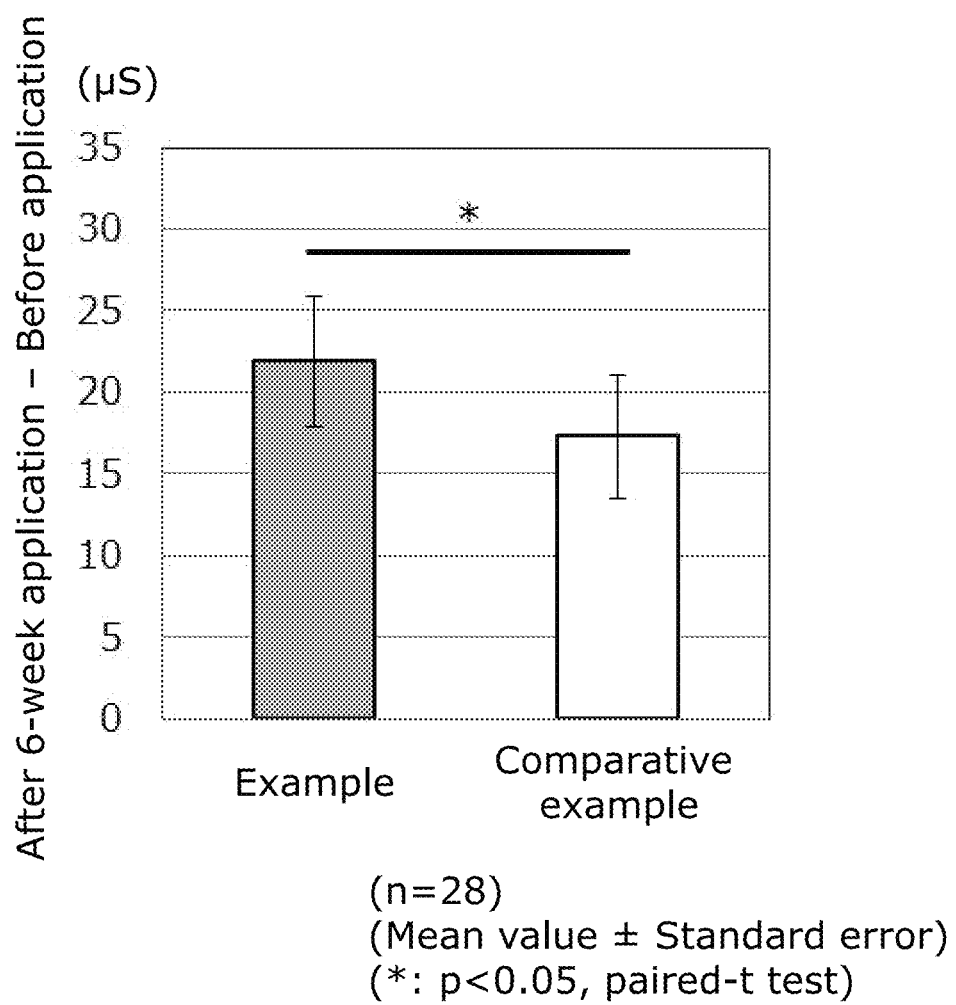
FIG. 3 is a graph showing the moisture content in the stratum corneum at a formulation application site.

The moisture contents of the stratum corneum at left and right cheeks were measured before and after the application period using a measurement device for an epidermal stratum corneum moisture content (SKICON; manufactured by IBS Ltd.), and the difference before the application and after the 6-week application was calculated. The mean values of all the test subjects are shown in FIG. 3 with respect to the cosmetics of the Example and Comparative Example. The larger value on the ordinate means a higher moisture content in the stratum corneum.

(4) Measurement Flexibility of Stratum Corneum.

Figure 4:
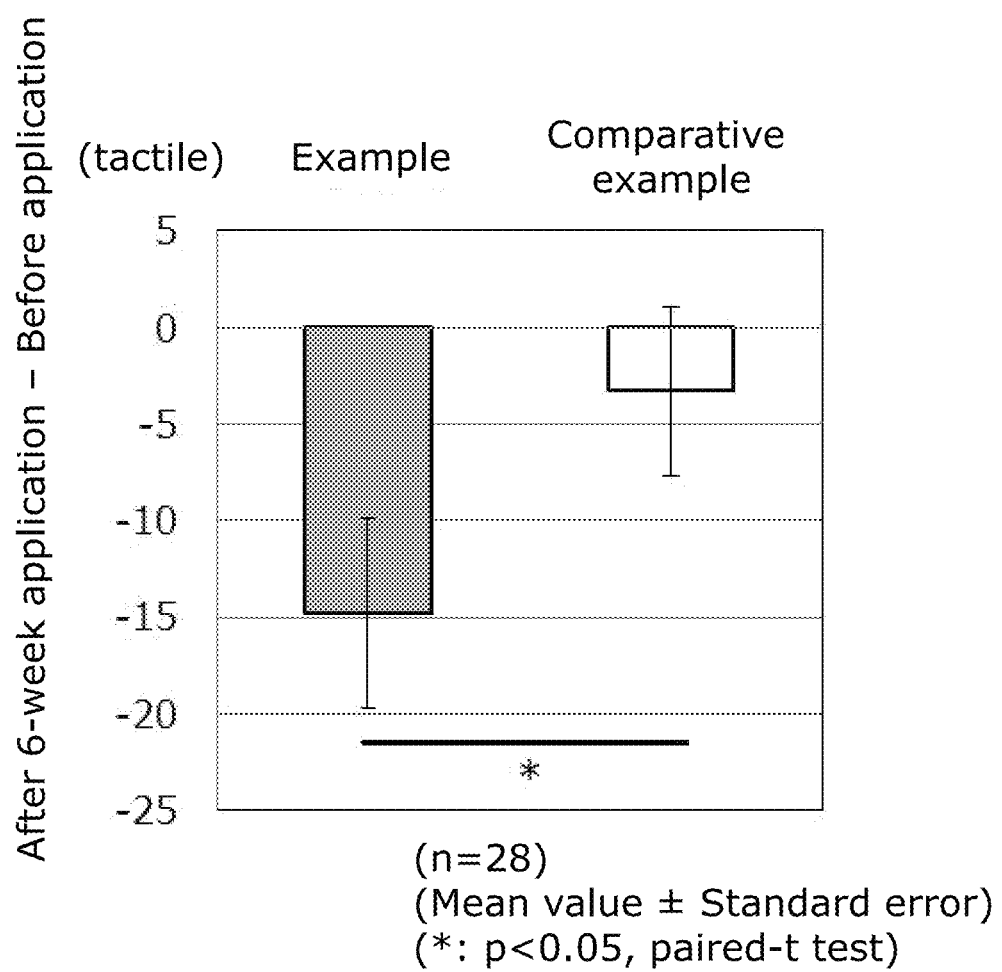
FIG. 4 is a graph showing the flexibility of the stratum corneum at a formulation application site.

The flexibility of the stratum corneum at left and right cheeks were measured before and after the application period using a measurement device (VENUSTRON; manufactured by Axiom Co., Ltd.) and the difference between before the application and after the 6-week application was calculated. The mean values of all the test subjects are shown in FIG. 4 with respect to the cosmetics of Example and Comparative Example. The smaller value on the ordinate means a higher flexibility of the stratum corneum.

At the application site of the cosmetic of Example, the differences between before application and after 6-week application in any of wrinkle grade rating, replica analysis, stratum corneum moisture content, and stratum corneum flexibility were significantly larger than those at the application site of the cosmetic of Comparative Example.

(5) Confirmation of Occurrence-Nonoccurrence of Adverse Event

Before and after the application period, a dermatologist examined by observation whether an adverse event such as reddening at a left and right cheek of the test subject was recognizable or not, and confirmed if there was an appeal of skin abnormality of the test subject. As a result, no adverse event, which was considered to be caused by the cosmetic of Example or Comparative Example, was observed in any of the subjects, and there was no appeal of skin abnormality.

<Moisture Absorbing Property Confirmation Test>

Compound 1 was precisely weighed in a 1 g weighing bottle, left in a desiccator with a humidity at 75% (a saturated aqueous solution of sodium chloride) in an open state, and stored at 25° C. The weight was measured from the start of the storage until 30 days thereafter, and the coefficient of moisture absorption was determined by the following formula. The results are shown in Table 2.

Coefficient of moisture absorption (%)=($M3-M2$)/($M2-M1$)×100

M1: The mass of the weighing bottle (g)

M2: The mass of the weighing bottle containing a sample at the start of the storage (g)

M3: The mass of the weighing bottle containing the sample after the storage (g)

TABLE 2

| | Storage time | | | | |
| --- | --- | --- | --- | --- | --- |
| | 1 day | 3 days | 7 days | 14 days | 30 days |
| Coefficient of moisture absorption (%) (mean value, n = 3) | 13.2 | 19.0 | 20.5 | 21.0 | 21.2 |

Compound 1 absorbed moisture during the first 7 days after the start of the storage thereby increasing the weight by 20.5%, and thereafter the weight increase slowed down. From the above results, moisture absorbing property by Compound 1 was confirmed.

<Test for Confirming Expression-Increasing Effect of Epidermal Hyaluronan Synthetase Gene>

Normal human epidermal keratinocyte (produced by Kurabo Industries Ltd.) was inoculated in a 24-well plate at 4×10 cells/well, and incubated overnight at 37° C. in a 5% $CO_2$ environment. The culture medium was exchanged with a medium containing 0.2% by mass of Compound 1, or glycerol (produced by Wako Pure Chemical Industries, Ltd.) and cultured at 37° C. in a 5% $CO_2$ environment for 24 hours.

Using a mRNA recovery kit (FastLane Cell SYBR Green Kit, produced by Qiagen N.V.), mRNA was extracted by a conventional method. Using a qPCR kit (One Step SYBR PrimeScript RT-PCR Kit II, produced by Takara Bio Inc.), the expression level of the hyaluronan synthetase gene (HAS 1) was analyzed by qPCR using ACTB as an internal standard (7500 Real-Time PCR System, produced by Applied Biosystems). Data analysis was carried out by the ΔΔCt method.

Figure 5:
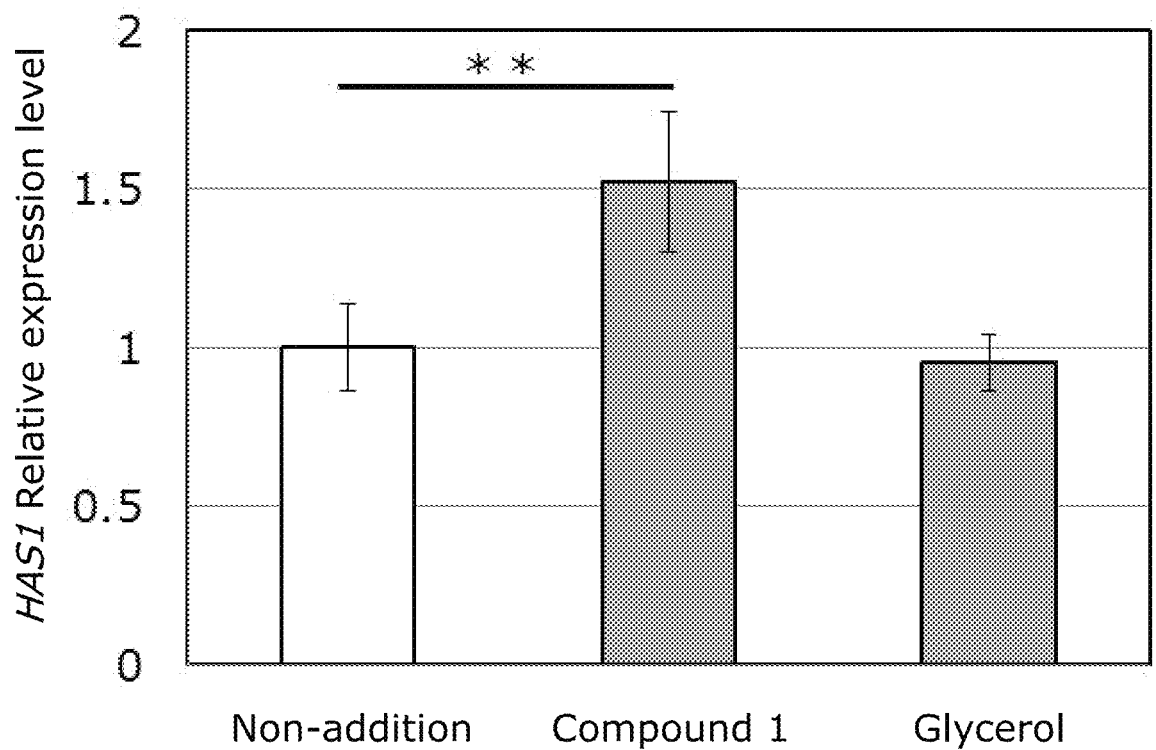
FIG. 5 is a graph showing a relative expression level of the hyaluronan synthetase gene (HAS1).

The respective relative values were calculated with respect to the expression level of the gene in a medium not containing Compound 1 and glycerol (non-addition group) as 1. The results are shown in FIG. 5.

In the group in which Compound 1 was added, the expression level of the hyaluronan synthetase gene (HAS 1) in normal human epidermal keratinocyte was significantly larger than that of the non-addition group. In the group in which the glycerol was added there was no significant difference compared to the non-addition group.

Production Example 1

A cosmetic lotion which was an external preparation for skin of the present invention was prepared according to the recipe shown in Table 3. That is, the ingredients of A were mixed at room temperature, and the ingredients of B were heated at 60° C. respectively and mixed together, then B was gradually added to A with stirring, and the mixture was cooled with stirring to yield a cosmetic lotion.

It was confirmed that this cosmetic lotion gave a wrinkle improvement effect when applied to the skin.

TABLE 3

| Cosmetic lotion | | |
| --- | --- | --- |
| | | (% by mass) |
| A | Poly(ethylene glycol) | 0.5 |
| | Glycerol | 10.0 |
| | Pentylene glycol | 2.0 |
| | Ethanol | 5.0 |
| | Diglycerol | 1.0 |
| | Citric acid | 0.1 |

TABLE 3-continued

Cosmetic lotion

|   |   | (% by mass) |
|---|---|---|
|   | Sodium citrate | 0.1 |
|   | Methylparaben | 0.2 |
|   | Phenoxyethanol | 0.2 |
|   | Pentasodium pentetate | 0.1 |
|   | Xanthan gum | 0.1 |
|   | Compound 1 | 0.5 |
|   | Water | Balance |
| B | 1,3-Butylene glycol | 5.0 |
|   | PEG-60 Hydrogenated castor oil | 0.1 |
|   | Sucrose laurate | 0.2 |
|   | Perfume | 0.2 |
|   | Total | 100.0 |

Production Example 2

A cosmetic lotion which was an external preparation for skin of the present invention was prepared according to the recipe shown in Table 4. That is, the ingredients of A were mixed at room temperature, and the ingredients of B were heated at 60° C. respectively and mixed together, then B was gradually added to A with stirring, and the mixture was cooled with stirring to yield a cosmetic lotion.

It was confirmed that this cosmetic lotion gave a wrinkle improvement effect when applied to the skin.

TABLE 4

Cosmetic lotion

|   |   | (% by mass) |
|---|---|---|
| A | Poly(ethylene glycol) | 0.5 |
|   | Glycerol | 10.0 |
|   | Pentylene glycol | 2.0 |
|   | Ethanol | 5.0 |
|   | Diglycerol | 1.0 |
|   | Citric acid | 0.1 |
|   | Sodium citrate | 0.1 |
|   | Methylparaben | 0.2 |
|   | Phenoxyethanol | 0.2 |
|   | Pentasodium pentetate | 0.1 |
|   | Xanthan gum | 0.1 |
|   | Compound 1 | 0.5 |
|   | Water | Balance |
| B | 1,3-Butylene glycol | 5.0 |
|   | PEG-60 Hydrogenated castor oil | 0.2 |
|   | Sucrose laurate | 0.2 |
|   | Glycerol tri(2-ethylhexanoate) | 1.0 |
|   | Perfume | 0.2 |
|   | Total | 100.0 |

Production Example 3

An essence which was an external preparation for skin of the present invention was prepared according to the recipe shown in Table 5. That is, the ingredients of A and B were heated at 80° C., and mixed together respectively, then B was gradually added to A with stirring, and the mixture was cooled with stirring to yield an essence.

It was confirmed that this essence gave a wrinkle improvement effect when applied to the skin.

TABLE 5

Essence

|   |   | (% by mass) |
|---|---|---|
| A | Poly(ethylene glycol) | 0.5 |
|   | Glycerol | 10.0 |
|   | Pentylene glycol | 2.0 |
|   | Ethanol | 5.0 |
|   | Diglycerol | 1.0 |
|   | Citric acid | 0.1 |
|   | Sodium citrate | 0.1 |
|   | Potassium hydroxide | 0.1 |
|   | Methylparaben | 0.2 |
|   | Phenoxyethanol | 0.2 |
|   | Pentasodium pentetate | 0.1 |
|   | Arbutin | 3.0 |
|   | Carbomer | 0.2 |
|   | Xanthan gum | 0.1 |
|   | Compound 1 | 0.5 |
|   | Dipotassium glycyrrhizinate | 0.1 |
|   | Water | Balance |
| B | 1,3-Butylene glycol | 5.0 |
|   | PEG-60 Hydrogenated castor oil | 0.1 |
|   | Sucrose laurate | 0.2 |
|   | Perfume | 0.2 |
|   | Total | 100.0 |

Production Example 4

A milky lotion which was an external preparation for skin of the present invention was prepared according to the recipe shown in Table 6. That is, the ingredients of A and B were heated at 80° C., and mixed together respectively, then B was gradually added to A with stirring, and the mixture was cooled with stirring to yield a milky lotion.

It was confirmed that this milky lotion gave a wrinkle improvement effect when applied to the skin.

TABLE 6

Milky lotion

|   |   | (% by mass) |
|---|---|---|
| A | Poly(ethylene glycol) | 0.5 |
|   | 1,3-Butylene glycol | 5.0 |
|   | Glycerol | 10.0 |
|   | Pentylene glycol | 2.0 |
|   | Ethanol | 5.0 |
|   | Diglycerol | 1.0 |
|   | Citric acid | 0.1 |
|   | Sodium citrate | 0.1 |
|   | Potassium hydroxide | 0.05 |
|   | Calcium chloride | 0.02 |
|   | Methylparaben | 0.2 |
|   | Phenoxyethanol | 0.2 |
|   | Pentasodium pentetate | 0.1 |
|   | Arbutin | 3.0 |
|   | Xanthan gum | 0.05 |
|   | Acrylate/(C10-30) alkyl acrylate) crosslinked polymer | 0.2 |
|   | Propylene glycol alginate | 0.5 |
|   | Fermented liquor of royal jelly | 0.5 |
|   | Compound 1 | 0.5 |
|   | Dipotassium glycyrrhizinate | 0.1 |
|   | Water | Balance |
| B | Mineral oil | 1.0 |
|   | Petrolatum | 0.5 |
|   | Microcrystalline wax | 0.5 |
|   | Cetyl ethylhexanoate | 1.0 |
|   | Glyceryl trioctanoate | 1.0 |
|   | Beeswax | 0.5 |
|   | Dimethicone | 0.5 |
|   | Methylphenylpolysiloxane | 0.5 |
|   | Sorbitan stearate | 0.1 |

TABLE 6-continued

Milky lotion

|  | (% by mass) |
| --- | --- |
| POE-20 sorbitan stearate | 0.1 |
| PEG-25 stearate | 0.1 |
| Sucrose stearate | 0.1 |
| Stearic acid | 0.1 |
| Cetanol | 0.5 |
| Perfume | 0.2 |
| Total | 100.0 |

Production Example 5

An O/W cream which was an external preparation for skin of the present invention was prepared according to the recipe shown in Table 7. That is, the ingredients of A and B were heated at 80° C., and mixed together respectively, then B was gradually added to A with stirring, and the mixture was cooled with stirring to yield an O/W cream.

It was confirmed that this O/W cream gave a wrinkle improvement effect when applied to the skin.

TABLE 7

O/W Cream

|  |  | (% by mass) |
| --- | --- | --- |
| A | Poly(ethylene glycol) | 0.5 |
|  | 1,3-Butylene glycol | 5.0 |
|  | Glycerol | 10.0 |
|  | Pentylene glycol | 2.0 |
|  | Ethanol | 2.0 |
|  | Diglycerol | 1.0 |
|  | Citric acid | 0.1 |
|  | Sodium citrate | 0.1 |
|  | Potassium hydroxide | 0.4 |
|  | Methylparaben | 0.2 |
|  | Phenoxyethanol | 0.2 |
|  | Pentasodium pentetate | 0.1 |
|  | Ascorbic acid glucoside | 2.0 |
|  | Xanthan gum | 0.05 |
|  | Acrylate/(C10-30) alkyl acrylate) crosslinked polymer | 0.2 |
|  | Compound 1 | 0.5 |
|  | Dipotassium glycyrrhizinate | 0.1 |
|  | Water | Balance |
| B | Mineral oil | 1.0 |
|  | Petrolatum | 0.5 |
|  | Microcrystalline wax | 0.5 |
|  | Cetyl ethylhexanoate | 1.0 |
|  | Glyceryl trioctanoate | 1.0 |
|  | Beeswax | 0.5 |
|  | Dimethicone | 0.5 |
|  | Methylphenyl polysiloxane | 0.5 |
|  | Sorbitan stearate | 0.5 |
|  | POE-20 sorbitan stearate | 0.5 |
|  | PEG-25 stearate | 0.5 |
|  | Sucrose stearate | 0.5 |
|  | Stearic acid | 0.5 |
|  | Cetanol | 1.0 |
|  | Behenyl alcohol | 0.5 |
|  | Ethylhexylglycerin | 0.2 |
|  | Tocopherol | 0.1 |
|  | Perfume | 0.2 |
| Total |  | 100.0 |

Production Example 6

A W/O cream which was an external preparation for skin of the present invention was prepared according to the recipe shown in Table 8. That is, the ingredients of A and B were heated at 80° C., and mixed together respectively, then A was gradually added to B with stirring, and the mixture was cooled with stirring to yield a W/O cream.

It was confirmed that this W/O cream gave a wrinkle improvement effect when applied to the skin.

TABLE 8

W/O Cream

|  |  | (% by mass) |
| --- | --- | --- |
| A | Poly(ethylene glycol) | 0.5 |
|  | 1,3-Butylene glycol | 5.0 |
|  | Glycerol | 15.0 |
|  | Pentylene glycol | 2.0 |
|  | Ethanol | 2.0 |
|  | Diglycerol | 1.0 |
|  | Citric acid | 0.1 |
|  | Sodium citrate | 0.1 |
|  | Methylparaben | 0.2 |
|  | Phenoxyethanol | 0.2 |
|  | Pentasodium pentetate | 0.1 |
|  | Ascorbic acid glucoside | 2.0 |
|  | Compound 1 | 0.5 |
|  | Dipotassium glycyrrhizinate | 0.1 |
|  | Water | Balance |
| B | Mineral oil | 1.0 |
|  | Petrolatum | 0.5 |
|  | Microcrystalline wax | 0.5 |
|  | Cetyl ethylhexanoate | 1.0 |
|  | Glyceryl trioctanoate | 1.0 |
|  | Beeswax | 0.5 |
|  | Dimethicone | 0.5 |
|  | Methylphenylpolysiloxane | 0.5 |
|  | Decamethylcyclopentasiloxane | 27.2 |
|  | Sucrose stearate | 0.5 |
|  | PEG-10 Dimethicone | 4.0 |
|  | Dimethyl distearyl ammonium hectorite | 2.0 |
|  | Ethylhexylglycerin | 0.2 |
|  | Tocopherol | 0.1 |
|  | Perfume | 0.2 |
| Total |  | 100.0 |

Production Example 7

An O/W foundation which was an external preparation for skin of the present invention was prepared according to the recipe shown in Table 9. That is, the ingredients of A and B were heated at 80° C., and mixed together respectively, then B was gradually added to A with stirring, and the mixture was cooled with stirring to yield an O/W foundation.

It was confirmed that this O/W foundation gave a wrinkle improvement effect when applied to the skin.

TABLE 9

O/W foundation

|  |  | (% by mass) |
| --- | --- | --- |
| A | Poly(ethylene glycol) | 0.5 |
|  | 1,3-Butylene glycol | 2.0 |
|  | Glycerol | 1.0 |
|  | Pentylene glycol | 2.0 |
|  | Ethanol | 1.0 |
|  | Diglycerol | 0.5 |
|  | Citric acid | 0.1 |
|  | Sodium citrate | 0.1 |
|  | Potassium hydroxide | 0.4 |
|  | Triethanolamine | 0.4 |
|  | Methylparaben | 0.2 |

TABLE 9-continued

O/W foundation

|  |  | (% by mass) |
|---|---|---|
|  | Phenoxyethanol | 0.2 |
|  | Pentasodium pentetate | 0.1 |
|  | Phenylbenzimidazole sulfonic acid | 0.5 |
|  | Ascorbic acid glucoside | 2.0 |
|  | Xanthan gum | 0.1 |
|  | Quince seed extract | 2.0 |
|  | Golden silk extract | 0.5 |
|  | Lotus extract | 0.5 |
|  | Royal jelly fermented liquor | 0.5 |
|  | Compound 1 | 0.5 |
|  | Water | Balance |
| B | Mineral oil | 5.0 |
|  | Petrolatum | 1.0 |
|  | Microcrystalline wax | 1.0 |
|  | Cetyl ethylhexanoate | 5.0 |
|  | Glyceryl trioctanoate | 1.0 |
|  | Hydrogenated rape oil | 1.0 |
|  | Beeswax | 1.0 |
|  | Dimethicone | 0.5 |
|  | Methylphenyl polysiloxane | 0.5 |
|  | Decamethylcyclopentasiloxane | 3.0 |
|  | Crosslinked dimethicone | 0.5 |
|  | t-Butyl methoxydibenzoylmethane | 1.0 |
|  | Ethylhexyl methoxycinnamate | 1.0 |
|  | Glyceryl oleate | 0.5 |
|  | Polyglyceryl oleate | 0.5 |
|  | Sorbitan isostearate | 1.0 |
|  | PEG-20 stearate | 0.5 |
|  | Sucrose stearate | 0.5 |
|  | Polyoxyethylene phytostanol | 0.5 |
|  | Polyoxyethylene polyglycerol stearyl ether | 0.5 |
|  | Stearic acid | 1.5 |
|  | Cetanol | 2.0 |
|  | Behenyl alcohol | 1.0 |
|  | (Alkyl acrylate/dimethicone) copolymer-treated and oxidized titanium | 9.0 |
|  | (Alkyl acrylate/dimethicone) copolymer-treated and oxidized Bengal red | 1.0 |
|  | (Alkyl acrylate/dimethicone) copolymer-treated and oxidized yellow iron oxide | 3.0 |
|  | (Alkyl acrylate/dimethicone) copolymer-treated and oxidized black iron oxide | 0.1 |
|  | Red No. 226 | 0.01 |
|  | Safflower red | 0.01 |
|  | Gardenia yellow | 0.01 |
|  | Gem Tone Ruby (produced by Engelhard Corp.) | 0.2 |
|  | Timiron Splendid Gold (produced by Merck & Co., Inc.) | 0.2 |
|  | Reflecks Pinpoints of Pearl (produced by Engelhard Corp.) | 0.2 |
|  | Trimethoxysilyl dimethicone-treated COLORONA GLITTER Bordeaux (produced by Merck & Co., Inc.) | 0.2 |
|  | Trimethoxysilyl dimethicone-treated GENESTAR 420 (produced by Nihon Koken Kogyo Co., Ltd.) | 0.2 |
|  | Trimethoxysilyl dimethicone-treated COVERLEAF MF (produced by JGC Catalysts and Chemicals Ltd.) | 0.2 |
|  | Perfluorooctyltriethoxysilane-treated COVERLEAF PC1035 (produced by JGC Catalysts and Chemicals Ltd.) | 0.2 |
|  | SILKYFLAKE FTD025FY-F02 (produced by Nippon Sheet Glass Co., Ltd.) | 0.2 |
|  | METASHINE MT1080KY (produced by Nippon Sheet Glass Co., Ltd.) | 0.2 |
|  | Talc | 3.0 |
|  | Fine particle titanium oxide ("MT-100SA", produced by Tayca Corporation) | 2.0 |
|  | Fine particle zinc oxide | 1.0 |
|  | Ethylhexylglycerin | 0.2 |
|  | Tocopherol | 0.1 |
|  | Perfume | 0.2 |
|  | Total | 100.0 |

Production Example 8

A W/O foundation which was an external preparation for skin of the present invention was prepared according to the recipe shown in Table 10. That is, the ingredients of A and B were heated at 80° C. and mixed together respectively, then A was gradually added to B with stirring, and the mixture was cooled with stirring to yield a W/O foundation.

It was confirmed that this W/O foundation gave a wrinkle improvement effect when applied to the skin.

TABLE 10

W/O foundation

|  |  | (% by mass) |
|---|---|---|
| A | Poly(ethylene glycol) | 0.5 |
|  | 1,3-Butylene glycol | 5.0 |
|  | Glycerol | 1.0 |
|  | Pentylene glycol | 2.0 |
|  | Ethanol | 1.0 |
|  | Diglycerol | 0.5 |
|  | Citric acid | 0.1 |
|  | Sodium citrate | 0.1 |
|  | Potassium hydroxide | 0.4 |
|  | Methylparaben | 0.2 |
|  | Phenoxyethanol | 0.2 |
|  | Pentasodium pentetate | 0.1 |
|  | Phenylbenzimidazole sulfonic acid | 0.5 |
|  | Ascorbic acid glucoside | 2.0 |
|  | Xanthan gum | 0.1 |
|  | Compound 1 | 0.5 |
|  | Water | balance |
| B | Mineral oil | 1.0 |
|  | Petrolatum | 0.5 |
|  | Microcrystalline wax | 0.5 |
|  | Cetyl ethylhexanoate | 1.0 |
|  | Glyceryl trioctanoate | 1.0 |
|  | Beeswax | 0.5 |
|  | Dimethicone | 0.5 |
|  | Methylphenylpolysiloxane | 1.0 |
|  | Decamethylcyclopentasiloxane | 14.0 |
|  | Crosslinked dimethicone | 0.5 |
|  | (Alkyl acrylate/dimethicone) copolymer | 0.5 |
|  | Trimethylsiloxysilicate | 0.5 |
|  | Caprylyl methicone | 0.5 |
|  | t-Butyl methoxybenzoylmethane | 1.0 |
|  | Ethylhexyl methoxycinnamate | 1.0 |
|  | Glyceryl oleate | 0.5 |
|  | Polyglyceryl oleate | 0.5 |
|  | Sorbitan isostearate | 0.5 |
|  | Sucrose stearate | 1.0 |
|  | Polyoxyethylene polyglycerol stearyl ether | 0.5 |
|  | PEG-10 Dimethicone | 3.0 |
|  | Dimethyl distearyl ammonium hectorite | 0.75 |
|  | (Alkyl acrylate/dimethicone) copolymer-treated and oxidized titanium | 8.0 |
|  | (Alkyl acrylate/dimethicone) copolymer-treated and oxidized Bengal red | 0.5 |
|  | (Alkyl acrylate/dimethicone) copolymer-treated and oxidized yellow iron oxide | 1.5 |
|  | (Alkyl acrylate/dimethicone) copolymer-treated and oxidized black iron oxide | 0.1 |
|  | Red No. 226 | 0.01 |
|  | Triethoxycaprylylsilane-treated Yellow No. 4 | 0.01 |
|  | Safflower red | 0.01 |
|  | Gardenia yellow | 0.01 |
|  | Gem Tone Ruby (produced by Engelhard Corp.) | 0.2 |
|  | Timiron Splendid Gold (produced by Merck & Co., Inc.) | 0.2 |
|  | Reflecks Pinpoints of Pearl (produced by Engelhard Corp.) | 0.2 |
|  | Trimethoxysilyl dimethicone-treated COLORONA GLITTER Bordeaux (produced by Merck & Co., Inc.) | 0.2 |
|  | Trimethoxysilyl dimethicone-treated GENESTAR 420 (produced by Nihon Koken Kogyo Co., Ltd.) | 0.2 |
|  | Trimethoxysilyl dimethicone-treated COVERLEAF MF (produced by JGC Catalysts and Chemicals Ltd.) | 0.2 |
|  | Perfluorooctyltriethoxysilane-treated COVERLEAF PC1035 (produced by JGC Catalysts and Chemicals Ltd.) | 0.2 |
|  | SILKYFLAKE FTD025FY-FOZ (produced by Nippon Sheet Glass Co., Ltd.) | 0.2 |
|  | METASHINE MT1080KY (produced by Nippon Sheet Glass Co., Ltd.) | 0.2 |

TABLE 10-continued

| W/O foundation | (% by mass) |
|---|---|
| Talc | 3.0 |
| Fine particle titanium oxide ("MT-100SA", produced by Tayca Corporation) | 1.0 |
| Fine particle zinc oxide | 0.5 |
| Ethylhexylglycerin | 0.2 |
| Tocopherol | 0.1 |
| Perfume | 0.2 |
| Total | 100.0 |

Production Example 9

An O/W sunscreen which was an external preparation for skin of the present invention was prepared according to the recipe shown in Table 11. That is, the ingredients of A and B were heated at 80° C., and mixed together respectively, then B was gradually added to A with stirring, and the mixture was cooled with stirring to yield an O/W sunscreen.

It was confirmed that this O/W sunscreen gave a wrinkle improvement effect when applied to the skin.

TABLE 11

| O/W Sunscreen | | (% by mass) |
|---|---|---|
| A | Poly(ethylene glycol) | 0.5 |
| | 1,3-Butylene glycol | 5.0 |
| | Glycerol | 1.0 |
| | Pentylene glycol | 1.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Triethanolamine | 0.4 |
| | Methylparaben | 0.2 |
| | Phenoxyethanol | 0.2 |
| | Pentasodium pentetate | 0.05 |
| | Phenylbenzimidazole sulfonic acid | 0.2 |
| | Ascorbic acid glucoside | 2.0 |
| | Xanthan gum | 0.1 |
| | Compound 1 | 0.5 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 4.0 |
| | Beeswax | 0.5 |
| | Dimethicone | 0.5 |
| | Methylphenylpolysiloxane | 0.5 |
| | Decamethylcyclopentasiloxane | 3.0 |
| | Crosslinked dimthicone | 0.5 |
| | (Alkyl acrylate/dimethicone) copolymer | 0.5 |
| | t-Butyl methoxydibenzoylmethane | 1.0 |
| | Ethylhexyl methoxycinnamate | 3.0 |
| | Glyceryl oleate | 0.5 |
| | Polyglyceryl oleate | 0.5 |
| | Sorbitan isostearate | 0.5 |
| | PEG-20 stearate | 0.5 |
| | Sucrose stearate | 0.5 |
| | Polyoxyethylene phytostanol | 0.5 |
| | Polyoxyethylene polyglycerol stearyl ether | 0.3 |
| | Na Cocomonoglyceride sulfate | 0.1 |
| | Na Stearoyl lactylate | 0.1 |
| | PEG-10 Dimethicone | 0.5 |
| | Stearic acid | 0.5 |

TABLE 11-continued

| O/W Sunscreen | (% by mass) |
|---|---|
| Cetanol | 1.0 |
| Behenyl alcohol | 0.5 |
| (Alkyl acrylate/dimethicone) copolymer-treated and oxidized titanium | 1.0 |
| (Alkyl acrylate/dimethicone) copolymer-treated and oxidized Bengal red | 0.5 |
| (Alkyl acrylate/dimethicone) copolymer-treated and oxidized yellow iron oxide | 0.1 |
| (Alkyl acrylate/dimethicone) copolymer-treated and oxidized black iron oxide | 0.01 |
| Red No. 226 | 0.01 |
| Triethoxycaprylylsilane-treated Yellow No. 4 | 0.01 |
| Safflower red | 0.01 |
| Gardenia yellow | 0.01 |
| Gem Tone Ruby (produced by Engelhard Corp.) | 0.1 |
| Timiron Splendid Gold (produced by Merck & Co., Inc.) | 0.1 |
| Reflecks Pinpoints of Pearl (produced by Engelhard Corp.) | 0.1 |
| Trimethoxysilyl dimethicone-treated COLORONA GLITTER Bordeaux (produced by Merck & Co., Inc.) | 0.1 |
| Trimethoxysilyl dimethicone-treated GENESTAR 420 (produced by Nihon Koken Kogyo Co., Ltd.) | 0.1 |
| Trimethoxysilyl dimethicone-treated COVERLEAF MF (produced by JGC Catalysts and Chemicals Ltd.) | 0.1 |
| Perfluorooctyltriethoxysilane-treated COVERLEAF PC1035 (produced by JGC Catalysts and Chemicals Ltd.) | 0.1 |
| SILKYFLAKE FTD025FY-F02 (produced by Nippon Sheet Glass Co., Ltd.) | 0.1 |
| METASHINE MT1080KY (produced by Nippon Sheet Glass Co., Ltd.) | 0.1 |
| Talc | 1.0 |
| Crosslinked methyl methacrylate polymer | 1.0 |
| Fine particle titanium oxide ("M1100SA", produced by Tayca Corporation) | 6.0 |
| Polyacrylate | 0.1 |
| Fine particle zinc oxide | 2.0 |
| Ethylhexylglycerin | 0.1 |
| Tocopherol | 0.05 |
| Perfume | 0.2 |
| Total | 100.0 |

Production Example 10

A W/O sunscreen which was an external preparation for skin of the present invention was prepared according to the recipe shown in Table 12. That is, the ingredients of A and B were heated at 80° C., and mixed together respectively, then A was gradually added to B with stirring, and the mixture was cooled with stirring to yield a W/O sunscreen.

It was confirmed that this W/O sunscreen gave a wrinkle improvement effect when applied to the skin.

TABLE 12

| W/O Sunscreen | | (% by mass) |
|---|---|---|
| A | Poly(ethylene glycol) | 0.5 |
| | 1,3-Butylene glycol | 5.0 |
| | Glycerol | 1.0 |
| | Pentylene glycol | 2.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Methylparaben | 0.2 |
| | Phenoxyethanol | 0.2 |

TABLE 12-continued

W/O Sunscreen

| | | (% by mass) |
|---|---|---|
| | Pentasodium pentetate | 0.1 |
| | Phenylbenzimidazole sulfonic acid | 0.5 |
| | Ascorbic acid glycoside | 2.0 |
| | Xanthan gum | 0.1 |
| | Compound 1 | 0.5 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenylpolysiloxane | 1.0 |
| | Decamethylcyclopentasiloxane | 14.0 |
| | Crosslinked dimethicone | 0.5 |
| | (Alkyl acrylate/dimethicone) copolymer | 0.5 |
| | Trimethylsiloxysilicate | 0.5 |
| | Caprylyl methicone | 0.5 |
| | t-Butyl methoxybenzoylmethane | 1.0 |
| | Ethylhexyl methoxycinnamate | 1.0 |
| | Glyceryl oleate | 0.5 |
| | Polyglyceryl oleate | 0.5 |
| | Sorbitan isostearate | 0.5 |
| | Sucrose stearate | 1.0 |
| | Polyoxyethylene polyglycerol stearyl ether | 0.5 |
| | PEG-10 Dimethicone | 3.0 |
| | Dimethyl distearyl ammonium hectorite | 0.75 |
| | (Alkyl acrylate/dimethicone) copolymer-treated and oxidized titanium | 8.0 |
| | (Alkyl acrylate/dimethicone) copolymer-treated and oxidized Bengal red | 0.5 |
| | (Alkyl acrylate/dimethicone) copolymer-treated and oxidized yellow iron oxide | 1.5 |
| | (Alkyl acrylate/dimethicone) copolymer-treated and oxidized black iron oxide | 0.1 |
| | Red No. 226 | 0.01 |
| | Triethoxycaprylylsilane-treated Yellow No. 4 | 0.01 |
| | Safflower red | 0.01 |
| | Gardenia yellow | 0.01 |
| | Gem Tone Ruby (produced by Engelhard Corp.) | 0.2 |
| | Timiron Splendid Gold (produced by Merck & Co., Inc.) | 0.2 |
| | Reflecks Pinpoints of Pearl (produced by Engelhard Corp.) | 0.2 |
| | Trimethoxysilyl dimethicone-treated COLORONA GLITTER Bordeaux (produced by Merck & Co., Inc.) | 0.2 |
| | Trimethoxysilyl dimethicone-treated GENESTAR 420 (produced by Nihon Koken Kogyo Co., Ltd.) | 0.2 |
| | Trimethoxysilyl dimethicone-treated COVERLEAF MF (produced by JGC Catalysts and Chemicals Ltd.) | 0.2 |
| | Perfluorohexylethyl trimethoxysilane-treated COVERLEAF PC1035 (produced by JGC Catalysts and Chemicals Ltd.) | 0.2 |
| | SILKYFLAKE FTD025FY-F02 (produced by Nippon Sheet Glass Co., Ltd.) | 0.2 |
| | METASHINE MT1080KY (produced by Nippon Sheet Glass Co., Ltd.) | 0.2 |
| | Talc | 3.0 |
| | Fine particle titanium oxide ("MT-100SA", produced by | 1.0 |

TABLE 12-continued

W/O Sunscreen

| | (% by mass) |
|---|---|
| Tayca Corporation) | |
| Fine particle zinc oxide | 0.5 |
| Ethylhexylglycerin | 0.2 |
| Tocopherol | 0.1 |
| Perfume | 0.2 |
| Total | 100.0 |

INDUSTRIAL APPLICABILITY

The wrinkle improving agent of the present invention has high safety to the skin and exhibits an excellent wrinkle improvement effect, and therefore it is extremely useful industrially, such that it can be suitably contained in an external composition for skin for wrinkle improvement.

The invention claimed is:

1. A method for wrinkle improving comprising applying to skin having wrinkles an agent comprising a compound expressed by one or more of the following Formulas (1) or (2);

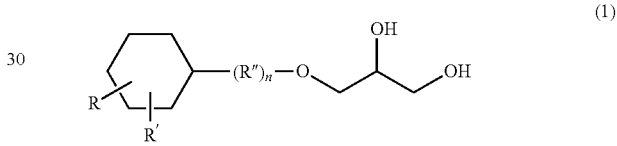

(1)

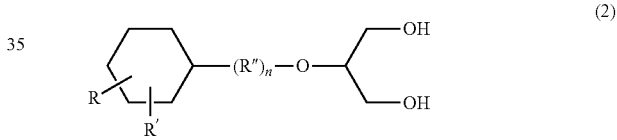

(2)

wherein in Formulas (1) and (2), R and R' independently represent a hydrogen atom or an alkyl group having 1 to 4 carbon atoms, R" represents an alkylene group having 1 to 3 carbon atoms, and n represents a number of 0 or 1.

2. The method according to claim 1, wherein the agent is contained in an external composition suitable for application to skin.

3. The method according to claim 2, wherein the external composition is a cosmetic formulation.

4. The method according to claim 1, wherein the wrinkles are improved by a hyaluronan synthesis promoting effect.

* * * * *